United States Patent [19]

Hosaka et al.

[11] 4,049,720
[45] Sept. 20, 1977

[54] PROCESS FOR PRODUCING β-ISOPROPYL-NAPHTHALENE HYDROPEROXIDE

[75] Inventors: Hirokazu Hosaka; Kenji Tanimoto, both of Minoo; Hiroshi Yamachika, Ibaraki, all of Japan

[73] Assignee: Sumitomo Chemical Company, Limited, Osaka, Japan

[21] Appl. No.: 551,812

[22] Filed: Feb. 21, 1975

[30] Foreign Application Priority Data

Feb. 21, 1974    Japan .................................. 49-21140

[51] Int. Cl.² ............................................ C07C 179/02
[52] U.S. Cl. .............................. 260/610 B; 260/624 R
[58] Field of Search ........... 260/610 B, 621 C, 590 R, 260/624 R

[56] References Cited

U.S. PATENT DOCUMENTS

| | | | |
|---|---|---|---|
| 2,771,491 | 11/1956 | Conner | 260/610 B |
| 2,776,322 | 1/1957 | Webster | 260/621 C |
| 2,850,548 | 9/1958 | Thelin | 260/621 C |
| 2,862,858 | 12/1958 | Conner | 260/621 C |

Primary Examiner—James O. Thomas, Jr.
Assistant Examiner—W. B. Lone
Attorney, Agent, or Firm—Sughrue, Rothwell, Mion, Zinn and Macpeak

[57] ABSTRACT

A process for the continuous production of β-isopropylnaphthalene hydroperoxide comprising oxidizing an isopropylnaphthalene mixture containing α- and β-isopropylnaphthalene isomers with molecular oxygen or a molecular oxygen containing gas in an oxidation zone and recycling unreacted ispropylnaphthalene recoverd after the oxidation to the oxidation zone, in which the oxidation is carried out by controlling the α-isopropylnaphthalene content in the isopropylnaphthalene mixture continuously fed to the oxidation zone to about 15% by weight or less.

4 Claims, 3 Drawing Figures

PROCESS FOR PRODUCING β-ISOPROPYL-NAPHTHALENE HYDROPEROXIDE

BACKGROUND OF THE INVENTION

1. Field of the Invention

The present invention relates to an industrially advantageous preparation of β-isopropylnaphthalene hydroperoxide, and more particularly to an industrially advantageous process for preparing β-isopropylnaphthalene hydroperoxide by oxidizing a mixture of isopropylnaphthalene isomers containing β-isopropylnaphthalene as a main component with oxygen or air, and recycling unreacted isopropylnaphthalene which is recovered at any step after the oxidation to the oxidation zone as a material for oxidation.

2. Description of the Prior Art

It is well known that β-naphthol is obtained by oxidizing β-ispropylnaphthalene (isopropylnaphthalene being hereinafter referred to as "IPN" for brevity) with oxygen or air and then subjecting the resulting β-ispropylnaphthalene hydroperoxide (isopropylnaphthalene hydroperoxide being hereinafter referred to as "NHPO" for brevity) to a catalytic cleavage in the presence of acidic catalysts.

The β-IPN, the material for oxidation is generally prepared by alkylation of naphthalene with propylene, and in the alkylation, α-IPN is always produced as a by-product under any conditions. Therefore, the material for oxidation is not pure β-IPN and, in general, contains a certain amount of α-IPN.

The oxidation of IPN is generally carried out by blowing molecular oxygen or an oxygen containing gas through an oil containing IPN, while the mixture is kept neutral to alkaline. On investigation of the oxidation process, it has now been found that all of the IPN, particularly the β-IPN contained therein, is practically impossible to oxidize completely for the reason that an increased conversion of IPN is followed by a reduction in oxidation rate of the remaining IPN whereby the total reaction time is prolonged, and that the prolonged reaction time (1) causes side-reactions to occur, for example, a conversion of the NHPO produced into a carbinol-type compound, thus remarkably reducing the yield of the NHPO, (2) allows the reaction system to become increasingly viscous thus making the handling of the reaction liquid increasingly difficult, and (3) at last leads to a serious problem from the standpoint of safety, such as handling of a very reactive highly concentrated hydroperoxide. Thus, it is most advantageous to stop the reaction when the NHPO concentration has reached about 10 to 40% by weight, from the standpoints of reaction time, yield of NHPO, handling of the reaction liquid and safety.

It is however very uneconomical due to a large loss of the starting material to carry out the oxidation with such a relatively low conversion and moreover without re-using the unreacted starting material, and therefore it is essential in an industrial scale production to recover the unreacted IPN after the oxidation and to recycle the unreacted IPN to the oxidation zone for reuse as a starting material.

Repeatedly recycling the unreacted IPN recovered results in a remarkable reduction in oxidation rate of β-IPN (consumption rate of β-IPN) which would not be expected from an oxidation using IPH which is prepared from naphthalene and propylene without use of the unreacted IPN recovered, so that the selectivity of β-IPN to β-NHPO (yield of β-NHPO based on the reacted β-IPN) is markedly decreased increasing the amount of by-products and decreasing the yield of β-NHPO and the quality of the β-naphthol as a final product. That is, it is very difficult to repeatedly recycle the unreacted IPN recovered to produce β-NHPO in an industrially advantageous manner where the IPN recovered is used as it is as a material for oxidation.

Research on the oxidation process has been conducted in order to overcome this difficulty, and it has now been found that a main factor hindering the oxidation is the presence of α-IPN, and further that β-NHPO can advantageously be prepared without a reduction in oxidation rate and selectively to β-NHPO by controlling the α-IPN content of the IPN mixture fed to the oxidation zone to about 15% by weight or less based on the weight of the IPN mixture.

SUMMARY OF THE INVENTION

Thus, the present invention provides a process for the continuous production of β-NHPO comprising oxidizing an IPN mixture containing α- and β-isomers and with molecular oxygen or a molecular oxygen-containing gas in an oxidation zone and recycling the unreacted IPN recovered after the oxidation, in which the α-IPN content of the IPN mixture continuously fed to the oxidation zone is controlled to about 15% by weight or less.

This invention also provides a process for the continuous production of β-naphthol, comprising the steps of (1) alkylating naphthalene with propylene to produce an IPN mixture, (2) oxidizing the resulting IPN mixture in an oxidation zone, (3) catalytically cleaving the resulting NHPO and (4) recycling the unreacted IPN recovered after the oxidizing (2) and/or the cleaving (3) to the oxidation zone, in which the α-IPN content in the IPN mixture continuously fed to the oxidation zone is controlled to about 15% by weight or less.

DETAILED DESCRIPTION OF THE INVENTION

The present invention is illustrated in greater detail below.

In the oxidation of the IPN mixture containing α- and β-isomers with molcular oxygen or air, the oxidation rate of α-IPN (consumption rate of α-IPN) is very different from the oxidation rate of β-IPN, and becomes about 1/5 to 1/10 times lower under the same oxidation conditions. This means that, in a continuous process wherein the IPN which is prepared from naphthalene and propylene is used as a starting material for the oxidation and the unreacted IPN recovered after the oxidation is recycled to the oxidation zone as it is, the α-IPN content in the IPN mixture increases with repeated recycling, that is, α-IPN accumulates increasingly in the IPN mixture. For example, when an IPN mixture containing an α-IPN content of about 5% by weight is used as a starting material for the oxidation, repeated recycling of the recovered IPN results in the final α-IPN content in the IPN mixture to reach as high as about 20 to 40% by weight.

In the process for production of β-NHPO, this accumulation of a α-IPN requires an increase in the size of the reaction vessel corresponding in volume to the useless α-IPN thus increasing the equipment cost, and therefore it makes the process very disadvantageous from an economical standpoint together with the above-described various disadvantages.

Figure 1:
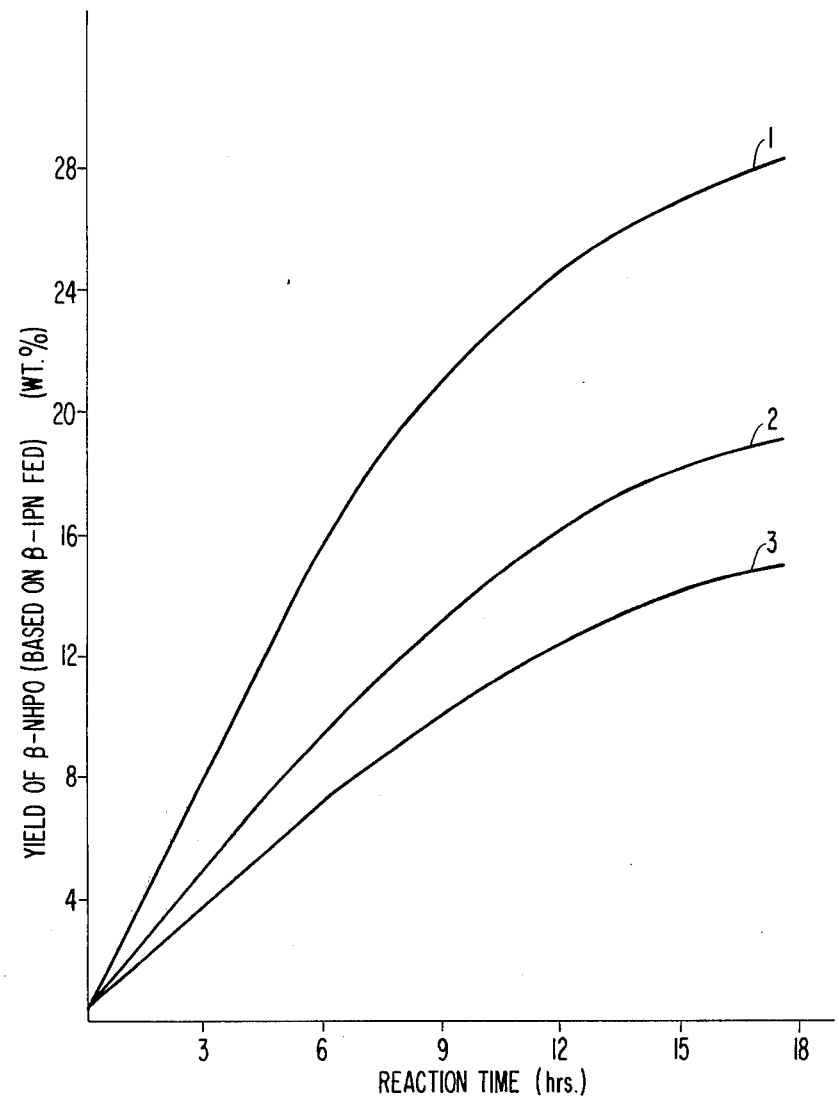
FIG. 1 shows the relationship between the reaction time (abscissa) and the yield of β-NHPO based on the β-IPN fed (ordinate) in the reaction using IPN mixtures having different α-IPN contents, 0, 20 and 30% by weight (Curves 1, 2 and 3 in the figure, respectively).
Figure 2:
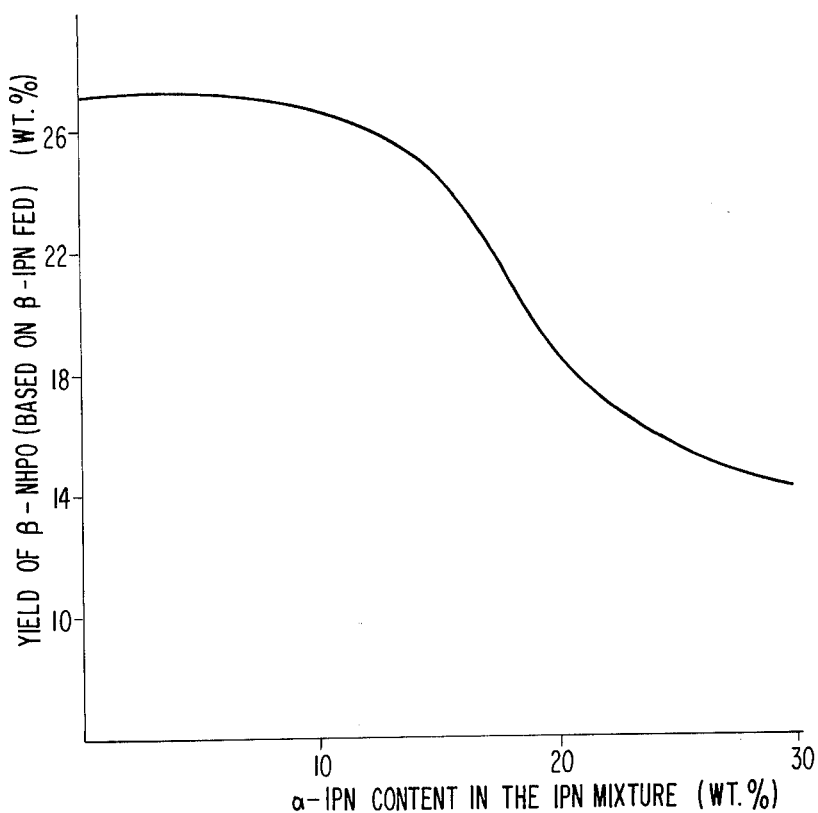
FIG. 2 shows the relationship between the α-IPN content of the total IPN 15 hours after the beginning of the reaction (abscissa) and the yield of β-NHPO based on the β-IPN fed (ordinate).

Furthermore, with respect to the relationship between α-IPN and β-IPN, it has been determined that α-IPN is not only oxidized very slowly but also interferes with the oxidation of β-IPN thereby reducing the oxidation rate and yield of β-NHPO from β-IPN as well. That is, when the oxidation is conducted using, as a starting material, IPN mixtures having different α-IPN contents, 0, 20 and 30% ( 1, 2 and 3 in FIG. 1, respectively) the yields of β-NHPO produced are as shown in FIG. 1. As can be seen from FIG. 1, the time required for β-NHPO to be produced in the same yield is more than two times longer in a mixture with an α-IPN content of 20% than in a mixture with an α-IPN content of 0 percent, that is, the reaction rate of the former mixture is reduced to less than half that of the latter mixture. Furthermore, the yield of β-NHPO decreases to a very low level as the α-IPN content increases, and the selectivity of β-IPN to β-NHPO alo decreases. For example, the selectivity is 88 percent for the mixture having an α-IPN content of 0 and 79 percent for the mixture having the α-IPN content of 20 percent, each β-NHPO concentration being 20 percent. This means that the higher the α-IPN content is, the larger is the amount of by-products other than β-NHPO produced from β-IPN. Thus, the α-IPN content has a very large effect on the oxidation. Moreover, the relationship between the α-IPN content and yield of β-NHPO is clear from the results obtained in an oxidation under the same condition using IPN-iosmer mixtures having different α-IPN contents, the results being as shown in FIG. 2. From these results in FIG. 2 it can be seen that the interference of α-IPN becomes remarkable when the α-IPN content exceeds 15 percent, but is very low at an α-IPN content of 15% by weight or less, that is, the oxidation rate is not very different between IPN mixtures having an α-IPN content of 15% by weight or less, while it is rapidly reduced at an α-IPN conent higher than 15% by weight. The same tendency is also observed for the selectivity of β-IPN to β-NHPO that is, the selectivity remains almost constant, 86 to 88 percent, at a α-IPN contents of 0 to 15% by weight, while the selectivity is remarkably reduced when the α-IPN content exceeds 15 percent.

As is apparent from the above explanation, for preparing β-NHPO in a high yield with a high reaction rate and without the interfering effect of α-IPN, it is very important to feed the IPN mixture in which the α-IPN content is constantly being kept at about 15% by weight or less.

In the present invention, recovery of the unreacted IPN can be carried out at any step after the oxidation, without particular limitation, depending on the production conditions, for example, at the end of the oxidation in which case the unreacted IPN is recovered from the oxidized oil by, for example, distillation or extraction, or at the end of the catalytic cleavage in which case the unreacted IPN is recovered from the cleavage product by, for example, rectification.

Furthermore, the α-IPN content of IPN mixtures which are fed to the oxidation zone can be reduced to about 15% by weight or less using any method depending on the production condition. For example, the unreacted IPN recovered can be removed partially to reduce the absolute amount of α-IPN and then mixed with fresh IPN containing a lower amount of α-IPN. Alternatively, the IPN prepared from naphthalene and propylene, and/or all or a part of the recovered IPN can be subjected to physical treatments such as crystallization and adsorption to remove all or a part of the α-IPN. While, the recovered IPN can be subjected to chemical treatments such as isomerization, for example, the recovered IPN can be recycled to the alkylation process for alkylation of naphthalene to convert the α-IPN to β-IPN.

Figure 3:
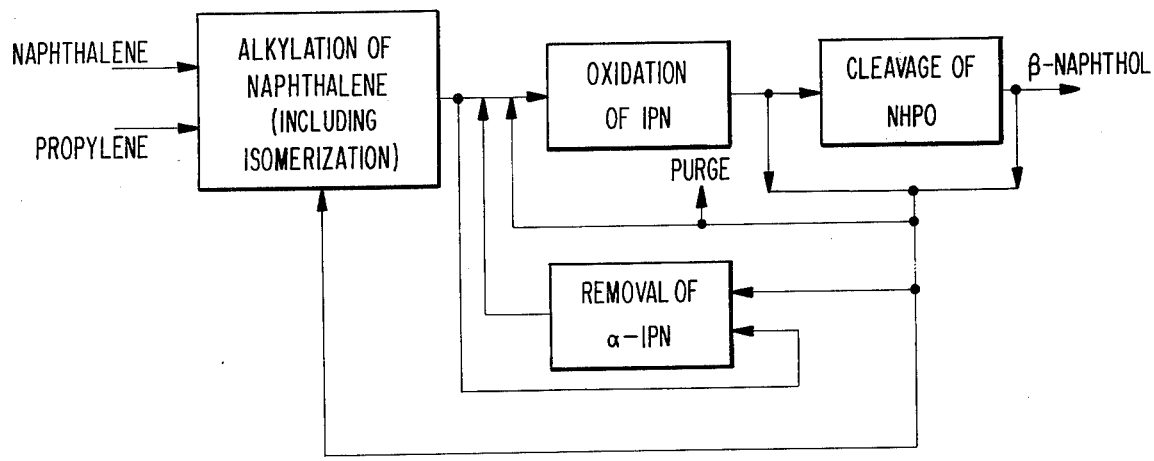
FIG. 3 shows a flow sheet of an embodiment of the invention.

One example of the recycle system according to the present invention is shown in FIG. 3.

The process according to the present invention including the oxidation reaction, the recovery of unreacted IPN and the recycle of recovered IPN can be carried out using a batchwise process, a continuous process or a combination thereof, depending on the production conditions.

In the oxidation reaction, the oily reaction zone is kept neutral to alkaline by adding inorganic alkalis, for example, hydroxides, carbonates or bicarbonates of sodium or potassium, preferably in the form of an aqueous solution, and the reaction is carried out at about 70° to 120° C while blowing molecular oxygen or an oxygen containing gas, e.g., air, through the reaction zone until the NHPO concentration approaches about 10 to 40% by weight.

As explained above, the present invention demonstrates that α-IPN contained in the IPN mixture has a marked interfering action on the oxidative formation of β-NHPO from β-IPN, and further that the action does not appear when the α-IPN content is reduced to about 15% by weight or less. Thus, by controlling the upper limit of the α-IPN content to about 15% without an unnecessary purification of the IPN mixture, the oxidation proceeds very easily, advantageously and moreover with the same results as obtained with high-purity β-IPN. Therefore, the present invention has great significance as an economical, industrial scale method of producing β-NHPO.

The present invention will be illustrated in greater detail by reference to the following examples which are only given for the purpose of illustration and the invention is not to be interpreted as being limited thereto. Unless otherwise indicated, all parts, percents, ratios and the like are by weight.

REFERENCE EXAMPLE 1

To a reaction vessel for continuous oxidation which had air-introduction equipment at the bottom, were fed continuously 1000 g/hr of IPN prepared from naphthalene and propylene (β-IPN : α-IPN = 95 : 5 on a weight basis, hereinafter referred to as "original IPN") and 500 g/hr of a 4% aqueous sodium hydroxide solution, thus a continuous oxidation was carried out at 90° C and with a retention time of 18 hours. As the oxidation proceeded, a mixture of the original IPN and the recovered IPN described hereinafter was used. The IPN was fed at a constant rate of 1,000 g/hr throughout the oxidation.

One hour after the recycle of recovered IPN to the oxidation zone was started, 1030 g/hr of the oxidized oil were obtained which contained 266 g of β-NHPO, 696 g of unreacted β-IPN, 1 g of α-NHPO and 48 g of α-IPN. Conversion $$(\frac{(\beta\text{-IPN Fed}) - (\beta\text{-IPN Remaining})}{\beta\text{-IPN Fed}} \times 100) \text{ of } \beta\text{-IPN:}$$
26.7% by weight.

$$\text{Yield } (\frac{\beta\text{-NHPO}}{\beta\text{-IPN Fed}} \times 100) \text{ of } \beta\text{-NHPO:}$$
28% by weight and selectivity.

$$(\frac{\beta\text{-NHPO}}{(\beta\text{-IPN Fed}) - (\beta\text{-IPN Remaining})} \times 100):$$
88% by mole.

The oxidized oil thus obtained was subjected to a continuous catalytic cleavage using a sulfuric acid catalyst during which NHPO was cleaved into naphthol and acetone, and then further subjected to a continuous rectification to recover 744 g/hr of the IPN mixture. The recovered IPN was recycled to the oxidation zone as described above. After the recycle was started, the feed of the original IPN was reduced by a feed of the recovered IPN in order to keep total IPN feed at a constant rate of 1,000 g/hr. The oxidation conditions after the beginning of the recycle were exactly the same as the above conditions. Table 1 shows the results of a 500 hour continuous oxidation reaction including the recycle of the recovered IPN.

It can be seen from the results in Table 1 that, when the recovered IPN is used as it is, the α-IPN content in the IPN mixtures fed to the oxidation increases gradually thus causing a marked reduction in a selectivity of β-IPN to β-NHPO and in the yield of β-NHPO.

isomerized above, β-IPN : α-IPN = 95 : 5 weight ratio), while keeping the total IPN feed at 1,000 g/hr.

When the oxidation reaction was carried out for 50 hours under the above-described operation conditions the α-IPN content of the total IPN fed was 12%. The oxidized oil obtained had the following composition: β-NHPO 238 g/hr, β-IPN 650 g/hr, α-NHPO 3 g/hr and α-IPN 115 g/hr. Conversion of β-IPN : 26.1% by weight. Yield of β-NHPO: 27% by weight, and selectivity of 87.1% by mole. Even after the oxidation was continuously carried out for an additional 300 hours, the α-IPN content was found to have been kept at a constant value of 12%, and the composition of the oxidized oil obtained, conversion of β-IPN and yield of β-NHPO from β-IPN were substantially unchanged.

While the invention has been described in detail and with reference to specific embodiments thereof, it will be apparent to one skilled in the art that various changes and modifications can be made therein without departing from the spirit and scope thereof.

What is claimed is:

1. In a process for the continuous production of β-isopropylnaphthalene hydroperoxide comprising oxidizing an isopropylnaphthalene mixture containing α- and β-isopropylnaphthalene isomers with molecular oxygen or a molecular oxygen containing gas at a temperature of about 70° to 120° C in an oxidation zone kept neutral to alkaline by adding an alkali selected from hydroxides, carbonates and bicarbonates of sodium and potassium until the isopropylnaphthalene hydroperoxide concentration reaches about 10 to 40% by weight and recycling unreacted isopropylnaphthalene recovered after the oxidation, wherein the α-isopropylnaphthalene content in the isopropylnaphthalene mixture continuously fed to the oxidation zone is controlled to be about 15% by weight or less.

Table 1

| | | Continuous Oxidation in Reference Example | | | | | |
|---|---|---|---|---|---|---|---|
| Reaction Time (1) (hr) | α-IPN Content of IPN Mixture (%) | Oxidized Oil | | | | Yield of* β-NHPO (% by weight) | Selectivity** to β-NHPO (% by mole) |
| | | β-NHPO (g/hr) | α-NHPO (g/hr) | β-IPN (g/hr) | α-IPN (g/hr) | | |
| 0 | 5.0 | 266 | 1 | 696 | 48 | 28.0 | 88 |
| 20 | 6.1 | 263 | 1 | 687 | 59 | 28.0 | 88 |
| 150 | 14.0 | 233 | 2 | 632 | 136 | 27.1 | 86 |
| 350 | 19.5 | 146 | 3 | 648 | 190 | 18.1 | 78 |
| 500 | 30.0 | 98 | 5 | 582 | 292 | 14.0 | 70.0 |

Note: (1) Reaction time elapsed after beginning of recycle of recovered IPN.

$$*\text{Yield } \beta\text{-NHPO} = \frac{\beta\text{-NHPO (wt.)}}{\beta\text{-IPN Fed (wt.)}} \times 100$$

$$**\text{Selectivity to } \beta\text{-NHPO} = \frac{\beta\text{-NHPO (mole)}}{(\beta\text{-IPN Fed}) - (\beta\text{-IPN Remaining}) \text{ (mole)}} \times 100$$

EXAMPLE 1

A continuous oxidation was carried out under the same conditions as described in Reference Example 1, except that the recovered IPN obtained by the continuous rectification was treated as follows before use for the recycle. A 10% portion of the recovered IPN was returned to an alkylation process for naphthalene with propylene and subjected to an isomerization of the α-IPN contained therein into β-IPN. The 90% portion remaining was directly recycled to the oxidation system together with the original IPN (containing the IPN 2. The process according to claim 1, wherein the controlling comprising subjecting the isopropylnaphthalene mixture and/or the recovered isopropylnaphthalene mixture to a crystallization or an adsorption to decrease the α-isopropylnaphthalene content prior to feeding to the oxidation zone.

3. The process according to claim 1, wherein the controlling comprising subjecting the unreacted isopropylnaphthalene recovered to an isomerization to decrease the α-isopropylnaphthalene content prior to recycling the unreacted isopropylnaphthalene recovered to the oxidation zone.

4. The process according to claim 1, wherein the controlling comprises recycling a part of the unreacted isopropylnaphthalene recovered to the oxidation zone.

* * * * *